US012778457B2

(12) United States Patent
Parikh

(10) Patent No.: US 12,778,457 B2
(45) Date of Patent: Nov. 3, 2026

(54) SENSORIZED BEAD-WIRE TOY FOR STUDYING FINGER FORCE AND MANUAL DEXTERITY

(71) Applicant: University of Houston System, Houston, TX (US)

(72) Inventor: Pranav J. Parikh, Richmond, TX (US)

(73) Assignee: University of Houston System, Houston, TX (US)

(*) Notice: Subject to any disclaimer, the term of this patent is extended or adjusted under 35 U.S.C. 154(b) by 875 days.

(21) Appl. No.: 17/962,597

(22) Filed: Oct. 10, 2022

(65) Prior Publication Data

US 2023/0121081 A1 Apr. 20, 2023

Related U.S. Application Data

(60) Provisional application No. 63/255,665, filed on Oct. 14, 2021.

(51) Int. Cl.
*A61B 5/11* (2006.01)
*A63H 33/00* (2006.01)
*G01L 1/22* (2006.01)

(52) U.S. Cl.
CPC .......... *A61B 5/1125* (2013.01); *A61B 5/1121* (2013.01); *A63H 33/00* (2013.01); *G01L 1/22* (2013.01); *A61B 2562/0252* (2013.01)

(58) Field of Classification Search
CPC ..... A61B 5/1125; A61B 5/1121; A61B 5/225; A61B 2562/0252; A61B 2562/0261; A63H 33/00; A63F 2007/4081; G01L 1/22
See application file for complete search history.

(56) References Cited

U.S. PATENT DOCUMENTS 5,551,933 A * 9/1996 Washburn .............. A63B 23/14 482/44
5,723,785 A * 3/1998 Manning ................ A63B 23/16 73/379.03

(Continued)

FOREIGN PATENT DOCUMENTS

GB 2 038 067 A 7/1980

OTHER PUBLICATIONS

International Search Report mailed Feb. 22, 2023 in International Patent Application No. PCT/US2022/046161 (2 pages).

(Continued)

*Primary Examiner* — Devin B Henson
(74) *Attorney, Agent, or Firm* — Smith, Gambrell & Russell, LLP

(57) ABSTRACT

A hand function testing device includes a base having a number of rigid wires protruding from a surface thereof, each rigid wire having a stationary bead affixed at a predetermined position along the rigid wire, a moving bead movably mounted on the rigid wire and movable along a working region of the rigid wire defined between a base-end of the rigid wire and the stationary bead, the moving bead being mounted on the rigid wire via reception of the rigid wire through a lumen in the moving bead, and at least one force sensing element for measuring a force input to the moving bead. A method of testing hand function includes using the hand function testing device to measure a force input to a moving bead as the moving bead is moved within a working region on the rigid wire.

47 Claims, 2 Drawing Sheets

(56) References Cited

U.S. PATENT DOCUMENTS

| | | | | |
|---|---|---|---|---|
| 8,547,328 | B2 | 10/2013 | Berkley et al. | |
| 9,084,565 | B2 | 7/2015 | Mason et al. | |
| 10,152,896 | B2 * | 12/2018 | Abadi | G09B 1/02 |
| 10,736,544 | B2 | 8/2020 | Cramer | |
| 2009/0111351 | A1 | 4/2009 | Krochak et al. | |
| 2010/0228156 | A1 * | 9/2010 | Valero-Cuevas | A63B 23/16 600/587 |
| 2016/0220863 | A1 * | 8/2016 | Braier | A63B 23/16 |
| 2017/0164900 | A1 * | 6/2017 | Johnson | A61B 5/7455 |

OTHER PUBLICATIONS

Written Opinion of the International Searching Authority mailed Feb. 22, 2023 in International Patent Application No. PCT/US2022/046161 (3 pages).

Duff, Susan V., et al. Innovative evaluation of dexterity in pediatrics. J Hand Ther. 2015. vol. 28(2): pp. 144-150.

Vollmer Brigitte, et al. Evidence of validity in a new method for measurement of dexterity in children and adolescents. Dev Med Child Neurol. 2010. vol. 52(10), pp. 948-954.

Valero-Cuevas Francisco J., et al. The strength-dexterity test as a measure of dynamic pinch performance. J Biomech. 2003. vol. 36(2), pp. 265-270.

Lawrence, Emily L., et al. Outcome measures for hand function naturally reveal three latent domains in older adults: strength, coordinated upper extremity function, and sensorimotor processing. Front Aging Neurosci. 2015. vol. 7(108), pp. 1-8.

Olsen, K.M., et al. Change in strength and dexterity after open carpal tunnel release. Int J Sports Med. 2001. vol. 22(4) pp. 301-303.

Sears, Erika Davis, et al. Validity and Responsiveness of the Jebsen-Taylor Hand Function Test. J Hand Surg Am. 2010. vol. 35(1), pp. 30-37.

Goodwin, A.W. Sensorimotor coordination in cerebral palsy. Lancet. 1999. vol. 353, pp. 2090-2091.

Parikh, Pranav J., et al. Dexterous object manipulation requires context-dependent sensorimotor cortical interactions in humans. Cereb Cortex. 2019. vol. 00, pp. 1-15.

Forssberg, H, et al. Development of human precision grip I: Basic coordination of force. Exp Brain Res. 1991. vol. 85, pp. 451-457.

Forssberg H, et al. Development of human precision grip—II. Anticipatory control of isometric forces targeted for object's weight. Exp Brain Res. 1992. vol. 90(2), pp. 393-398.

Gordon, Andrew M., et al. Fingertip forces during object manipulation in children with hemiplegic cerebral palsy. II: Bilateral coordination. Dev Med Child Neurol. 1999. vol. 41(3) pp. 176-185.

Cole, Kelly J. et al. Slowing of dexterous manipulation in old age: force and kinematic findings from the 'nut-and-rod' task. Exp Brain Res. 2010. vol. 201(2), pp. 239-247.

Parikh, Pranav J., et al. Handling objects in old age: forces and moments acting on the object. J Appl Physiol. 2012. vol. 112(7), pp. 1095-1104.

Gordon, Andrew M., et al. Fingertip force planning during grasp is disrupted by impaired sensorimotor integration in children with hemiplegic cerebral palsy. Pediatr Res. 2006. vol. 60(5), pp. 587-591.

Duff, Susan V., et al. Learning of grasp control in children with hemiplegic cerebral palsy. Dev Med Child Neurol. 2003. vol. 45(11), pp. 746-757.

Davare, Marco, et al. Sensorimotor uncertainty modulates corticospinal excitability during skilled object manipulation. J Neurophysiol. 2019. No. 121. pp. 1162-1170.

Parikh, Pranav J., et al. Effects of Transcranial Direct Current Stimulation on the Control of Finger Force during Dexterous Manipulation in Healthy Older Adults. PLOS One. 2015. vol. 10(4), pp. 1-10.

Parikh, Pranav J., et al. Effects of transcranial direct current stimulation in combination with motor practice on dexterous grasping and manipulation in healthy older adults. Physiol Rep. 2014. vol. 2(3), pp. 1-10.

Parikh. Pranav J., et al. Limited persistence of the sensorimotor memory when transferred across prehension tasks. Neurosci Lett. 2011. vol. 494(2), pp. 94-98.

Parikh, Pranav J., et al. Role of human premotor dorsal region in learning a conditional visuomotor task. J Neurophysiol. 2017. vol. 117, pp. 445-456.

Latash, Mark L., et al. Why did Grandpa drop the glass? J Appl Physiol. 2012. vol. 112(7), pp. 1093-1094.

* cited by examiner

SENSORIZED BEAD-WIRE TOY FOR STUDYING FINGER FORCE AND MANUAL DEXTERITY

FEDERALLY SPONSORED RESEARCH OR DEVELOPMENT

The present invention was made with government support under grant number P2CHD101899, awarded by the NIH/NICHD C-STAR, at Shirley Ryan AbilityLab. The US government has certain rights in the present invention.

FIELD OF THE INVENTION

The present invention relates to devices and methods for testing hand function. In particular, the present invention is directed to devices and methods that measure dynamic forces exerted on a hand manipulated object, as well as a time-based measure of such forces, for use in clinical diagnostic and therapeutic applications.

BACKGROUND OF THE INVENTION

Accurate hand sensorimotor function is important for the performance of day-to-day tasks that require dexterity. Fine hand motor control requires intact sensory information from the fingertips and the ability to execute motor commands, as well as the ability to integrate sensory information with motor commands (i.e. sensorimotor integration). Successful sensorimotor integration is the hallmark of hand function, and is responsible for critical aspects of manual function, such as precise motor control of force magnitude and direction of forces exerted by each digit on an object, as well as the ability to resist disturbances relayed on the hand-held object due to other digits and the environment.

An assessment of hand function measures a subject's skill in performing tasks with their hands. Hand function measurements of children may also be of clinical significance for identifying developmental pathologies, guiding treatments, and quantifying post-treatment progress. For example, a child's development or rehabilitation following a clinical treatment may be assessed by comparing the child's hand function performance to a baseline established from age normative data.

The most common pediatric dexterity tests include the Box and Block test, BOT-2 or Bruininks-Oseretsky Test of Motor Proficiency Ed. 2, PDMS-2 or Peabody Development Motor Scales Second Edition, the Shriners Hospital Upper Extremity Evaluation (SHUEE), Assisting Hand Assessment (AHA), Jebsen-Taylor Hand Function (JHFT) test, Functional Dexterity test (FDT), the ABILHAND-Kids, the Melbourne Assessment of Unilateral Upper Limb Function, the Quality of Upper Extremity Skills Test (QUEST), and Purdue Pegboard test. Most tests are extensive and take a considerable amount of time and expertise to administer and thus do not accommodate the short attention span of children with a wide range of cognitive and physical abilities. Some of these tests such as BOT-2, PDMS-2, QUEST, SHUEE, The Melbourne Assessment of Unilateral Upper Limb Function, and AHA provide a qualitative assessment of performance through observation (i.e., using a rating scale). However, they fail to quantify the quality of manual performance, and thus do not provide a truly objective assessment of dexterity. Other tests such as the Box and Block test, JTHFT, FDT, the Purdue Pegboard test focus on time-based measures of dexterity.

Time-based tests reflect on multiple aspects of motor control such as pre-shaping of the hand, grasping, transporting, releasing an object, strength, functional adaptations, eye-hand coordination, and the overall upper extremity movement. However, these measures are only a subset of functions necessary to manual activities, and do not account for information concerning the forces that a subject exerts on an object. Importantly, these conventional tests are also not sufficiently sensitive to identify subtle deficiencies in developmental hand function or small changes in hand function that may follow a clinical treatment.

A number of conventional Laboratory-based tests have attempted to quantify the development of digit force control in pediatric populations using sensors for measuring grip and load forces. Through a series of experiments, it was shown that at about two years of age children start demonstrating an adult-like grip and load force coordination strategy that continues to develop with age. By about eight years of age, the force coordination strategy nearly matches that observed in typically developed adults. It has also been shown that children with hemiplegia due to cerebral palsy have an impaired ability to coordinate their grip and load forces when compared with typically developing children. This impaired ability has been observed to improve, although not fully, with treatment. Further experiments have indicated that poor dexterity in children with cerebral palsy is due to impaired sensorimotor integration for digit force control. Conducting such a test in a clinical setting would be challenging. This test uses objects that are unfamiliar to children and therefore would require practice and extensive instructions. As a result, such a fine manual dexterity test may not be appropriate to assess children with short attention spans and those with a wide range of cognitive and physical abilities.

Thus, there remains a need for a device and method that provides a sensitive assessment of hand function in children, to measure the quality and control of movement (i.e., precision force control), and which is capable of doing so in a time efficient manner that is also effective for detecting deviations from the child's age norms.

SUMMARY OF THE INVENTION

A hand function testing device according to the present invention includes a base having a number of rigid wires protruding from a surface thereof, with each rigid wire being further provided with: a stationary bead affixed at a predetermined position along the rigid wire; a moving bead movably mounted on the rigid wire and movable along a working region of the rigid wire defined between a base-end of the rigid wire and the stationary bead, the moving bead being mounted on the rigid wire via reception of the rigid wire through a lumen in the moving bead; and at least one force sensing element for measuring a force input to the moving bead while the moving bead is moved within the working region of the rigid wire.

The hand function testing device may be provided with one, two or three or more rigid wires. When there are multiple rigid wires, each rigid wire will have a different configuration from one another based on differences in at least one of: a difference in shape of the rigid wires; a difference in positioning of a stationary bead at positions along the rigid wires; a combination of difference in shape and positioning of a stationary bead.

The at last one force sensing element may be any of a force sensing element positioned at the base-end of the rigid wire and adapted to measure a force input to the moving bead based on the transmission of an input force to the moving bead and through the rigid wire (e.g., a strain-gauge based load cell transducers); a force sensing element embedded in the surface of the moving bead and adapted to directly measure a force applied to a surface of the moving bead (e.g., a force-sensing flexible resistor); or a force sensing element embedded internally within the moving bead and adapted to directly measure a force applied to the moving bead based on a change in an electromagnetic field (e.g., an electromagnetic sensor). Any combination of two or more of the foregoing sensing elements may be employed. Preferably, the one or more force sensing elements are adapted to measure a force input to the moving bead in three separate axes.

In use, a subject moves a moving bead along a corresponding rigid wire, and force inputs to the moving bead are measured while the moving bead is moved within a working region defined between the base-end of the rigid wire and the stationary bead mounted thereon. The force input is measured over a period of time spanning from an initial bead contact up to a bead-to-bead impact, the initial bead contact corresponding with detection of a first force input to the moving bead following a state of rest, and the bead-to-bead impact corresponding with a first detected contact of the moving bead with a stationary bead. Preferably, measurements are made for force inputs to at least two separate moving beads on at least two separate rigid wires, each rigid wire having a different configuration from one another.

When the hand function testing device is adapted to communicate with a separate system for transmitting, recording, and/or assessing test results, then use of the hand function testing device further includes receiving the measurements of force inputs to the one or more moving beads on the one or more rigid wires at the separate system, the received force measurements informing of force input for moving the one or more moving beads within a working region of the one or more rigid wires.

Both the foregoing general description and the following detailed description are exemplary and explanatory only and are intended to provide further explanation of the invention as claimed. The accompanying drawings are included to provide a further understanding of the invention; are incorporated in and constitute part of this specification; illustrate embodiments of the invention; and, together with the description, serve to explain the principles of the invention.

BRIEF DESCRIPTION OF THE DRAWINGS

Further features and advantages of the invention can be ascertained from the following detailed description that is provided in connection with the drawings described below.

DETAILED DESCRIPTION OF THE INVENTION

Figure 1:
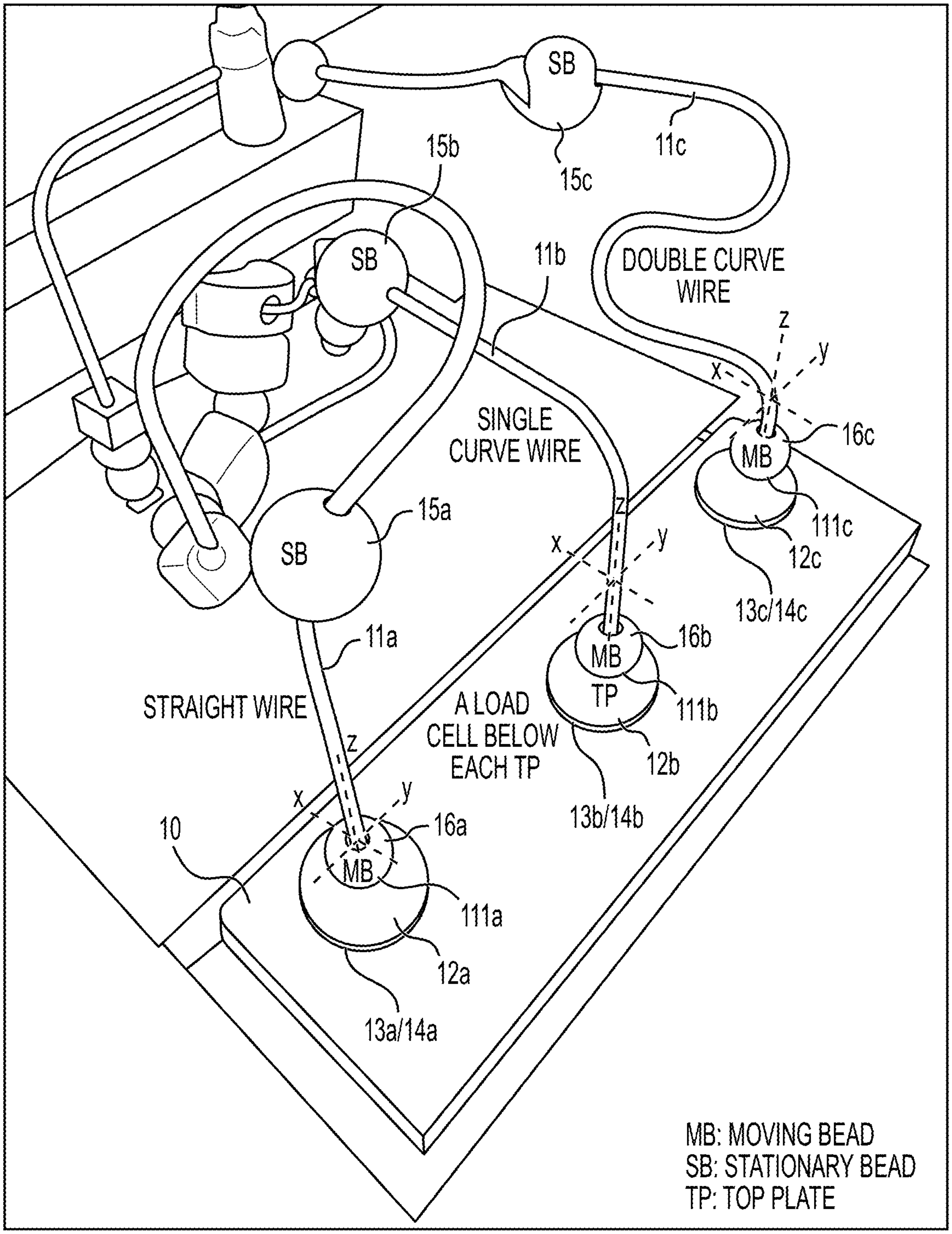
FIG. 1 shows an example of a hand function testing device according to the present invention.

The following disclosure discusses the present invention with reference to the examples shown in the accompanying drawings, though does not limit the invention to those examples.

The use of any and all examples, or exemplary language (e.g., "such as") provided herein is intended merely to better illuminate the invention and does not pose a limitation on the scope of the invention unless otherwise claimed. No language in the specification should be construed as indicating any non-claimed element as essential or otherwise critical to the practice of the invention, unless otherwise made clear in context.

As used herein, the singular forms "a," "an," and "the" include plural referents unless the context clearly dictates otherwise. Unless indicated otherwise by context, the term "or" is to be understood as an inclusive "or." Terms such as "first", "second", "third", etc. when used to describe multiple devices or elements, are so used only to convey the relative actions, positioning and/or functions of the separate devices, and do not necessitate either a specific order for such devices or elements, or any specific quantity or ranking of such devices or elements.

The word "substantially", as used herein with respect to any property or circumstance, refers to a degree of deviation that is sufficiently small so as to not appreciably detract from the identified property or circumstance. The exact degree of deviation allowable in a given circumstance will depend on the specific context, as would be understood by one having ordinary skill in the art.

Use of the terms "about" or "approximately" are intended to describe values above and/or below a stated value or range, as would be understood by one having ordinary skill in the art in the respective context. In some instances, this may encompass values in a range of approx. +/−10%; in other instances, there may be encompassed values in a range of approx. +/−5%; in yet other instances values in a range of approx. +/−2% may be encompassed; and in yet further instances, this may encompass values in a range of approx. +/−1%.

It will be understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof, unless indicated herein or otherwise clearly contradicted by context.

The terms "individual", "host", "subject", and "patient", as may be used interchangeably herein, refer to a mammal, including, but not limited to, primates, for example, human beings, as well as rodents, such as mice and rats, and other laboratory animals. References herein to "children" will also be understood as interchangeable with the foregoing terms.

Recitations of value ranges herein, unless indicated otherwise, serve as shorthand for referring individually to each separate value falling within the respective ranges, including the endpoints of the range, each separate value within the range, and all intermediate ranges subsumed by the overall range, with each incorporated into the specification as if individually recited herein.

Unless indicated otherwise, or clearly contradicted by context, methods described herein can be performed with the individual steps executed in any suitable order, including: the precise order disclosed, without any intermediate steps or with one or more further steps interposed between the disclosed steps; with the disclosed steps performed in an order other than the exact order disclosed; with one or more steps performed simultaneously; and with one or more disclosed steps omitted.

The present invention is inclusive of diagnostic and therapeutic devices and methods that task a subject (e.g., a child) with manipulating an object by hand, and measure dynamic precision control of digit forces exerted on the object during performance as well as a time-based measure for performance of the task. Generally, the child is tasked with moving a number of small objects from corresponding first locations to second locations and performing these tasks under three separate difficulty conditions of low, medium, and high. The child's performance is measured to obtain a comprehensive assessment for use in detecting deviations in the child's development, which may include an assessment as to the effectiveness of a prior clinical treatment and the child's development or rehabilitation following such treatment. A child's performance is assessed by comparison to a baseline established from normative data for their age range.

An example of a hand function testing device 100, in the form of a bead-wire device, is shown in FIG. 1. In this example, the device 100 has a base 10 that measures approximately 260 mm by approximately 100 mm in size, and is provided with a combination of straight and curved rigid metal wires 11 that are each attached to the base 10 via a corresponding interface top plate (TP) 12 that measures approximately 34 mm in diameter. Tri-axial strain-gauge based load cell transducers 13 are mounted on the base 10, at the base-ends 111 of each wire 11. Each load cell transducer 13 is affixed to the base 10, below a corresponding top plate 12, using a bottom plate (BP) 14 that measures approximately 50 mm in diameter. With this arrangement, the load cell transducers 13 are each configured for monitoring forces applied to and transmitted through the corresponding wires 11, including forces along each of a vertical axis (Z) and a pair of horizontal axes (X,Y).

The device 100 uses a number of wires 11 of different shapes. The wires 11 are made of polished steel with a diameter of 4 mm and are oriented to extend generally vertically from the corresponding top plates 12, and may optionally be colored coded. Each wire 11 is provided with both a stationary bead (SB) 15 that is statically affixed to the respective wire 11 and a moving bead (MB) 16 that is movably mounted on the respective wire 11 for sliding along the wire 11 under manipulation of a child. In the illustrated example, the stationary beads 15 have an outer diameter of 24 mm, and the moving beads 16 have an outer diameter of 18 mm. The moving beads 16 each have a lumen passing through a center thereof for sliding reception of the corresponding wire 11, the lumen having a diameter of 6.5 mm. The measurements from this example are non-limiting, and may be varied as needed. The measurements of the beads may also vary from one another in a single construction. For example, the outer diameter of the various beads may be made to vary from one another to provide differences in a required gripping force from one bead to another; this may be especially desirable for the moving beads 16 that are to be gripped by a child. Likewise, the lumen diameter of the moving beads 16 may be made to vary from one another to provide differences in a required force for translating a moving bead 16 along a wire 11. Preferably, the outer surfaces of the moving beads 16 are provided with a textured surface that minimizes accidental/unwanted slippage, so as to provide a more accurate testing of a child's grip and manipulation of the bead itself.

The several wires 11 in the device 100 are each provided with varying configurations, based on the shape of the wire 11 itself as well as the positioning of the stationary beads 15 along the wire 11. The complexity of the task in translating a moving bead 16 along a wire 11 will be determined based on both these factors. The region of a wire 11 along which a moving bead 16 may be translated may also be referred to as a working region. In the illustrated example, a first wire **11*a* is provided with a stationary bead 15*a* positioned approximately 100 mm from a base-end 111*a* at the corresponding top plate 12*a* to define a working region of a single length extending straight in a single direction, thereby defining a so-called "straight wire" of relatively low complexity. A second wire 11*b* is provided with a stationary bead 15*b* positioned approximately 170 mm from the base-end 111*b* at the corresponding tope plate 12*b* to define a working region with a single curve that divides the wire 11*b* into two separate lengths, thereby defining a so-called "single curve wire" of relatively medium complexity. A third wire 11*c* is provided with a stationary bead 15*c* positioned approximately 300 mm from the base-end 111*c* at the corresponding top plate 12*c* to define a working region with multiple curves, specifically three curves in this instance, that divide the wire 11*c* into three separate lengths, thereby defining a so-called "multi-curve wire" of relatively high complexity. In the illustrated example, the base-ends 111 of the three wires 11** are spaced approximately 90 mm apart.

Optionally, each moving bead 16 and/or stationary bead 15 may be provided with a force-sensing flexible resistor embedded under the outer surface. When provided, such surface-embedded resistors may directly measure a pressure that a child applies on a moving bead 16, and/or a contact force between a moving bead 16 and a stationary bead 15. As a further option, each moving bead 16 may be provided with an internal electromagnetic sensor for tracking a motion of the bead along the corresponding wire 11.

In some example, the device 100 may be made with multiple beads provided on a single wire; variations to surface texture and/or dimensions of the beads and/or wires; variations in outer diameter of beads and/or wires; variations in the dimensions of the lumens in the beads; and any combination of the foregoing. In some examples, the device 100 may also be provided with a motivational feedback system that further incentivizes children to interact with the device. For example, the device 100 may be made with one or more contact sensors provided in one or more moving beads 16 and/or a stationary beads 15 that is in communication with a sensory feedback system that is adapted for providing feedback to a user of the device 100 by outputting one or more of an audio signal (e.g., musical and/or other sound recordings), a visual signal (e.g., one or more lights of various colors and sequences, and/or other graphical displays), and/or a somatosensory signal (e.g., a vibration of one or more components of the device) upon contact of a moving bead 16 with a stationary bead 15. The device 100 may be further configured to enable intensity modulation of the feedback signals output by the sensory feedback system, for example, with one or more of an "OFF" setting in which no feedback signals are output, and "LOW", "MEDIUM" and "HIGH" settings in which signals of respective low, medium and high intensities are output.

The load cell transducers 13, as well as any other optional sensing elements (e.g., surface embedded force sensors, internal electromagnetic sensors, etc.), will transmit measured data to a non-transitory storage medium that stores the data for subsequent analysis. The sensing elements may transmit data through any suitable connection, including wired or wireless, and any suitable program may be used for acquiring transmitted data (e.g., LabVIEW VI, National Instruments, etc.) and analyzing stored data (e.g., a custom-written script in MATLAB (R2020b)).

Figure 2:
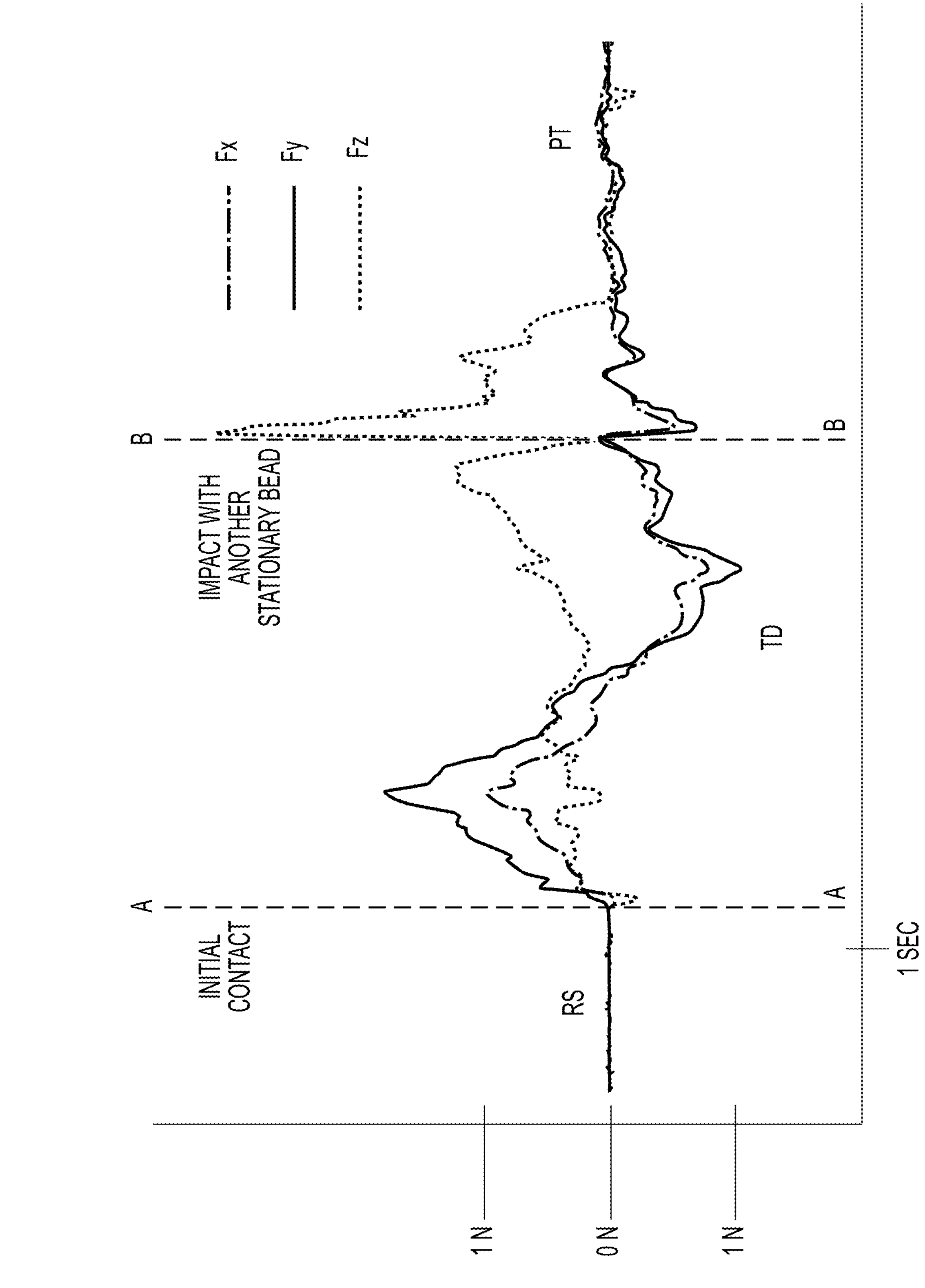
FIG. 2 shows force measurements acquired from a hand function test using the device of FIG. 1.

The device 100 may acquire a number of measurements of a child's performance in manipulating the moving beads 16 on the respective wires 11, including: a total force applied to the individual beads; a trial duration; and a force impulse (total force applied over the trial duration). FIG. 2 shows one example of a force analysis generated during a single trial duration of a child's manipulation of a moving bead 16 on a corresponding wire 11. In the illustrated example, a line A-A identifies an initial bead contact, corresponding with detection of a force informing when a child first contacts a moving bead 16 on a wire 11; and a line B-B identifies a final bead-to-bead impact, corresponding with a first occurrence of a contact between a moving bead 16 and a corresponding stationary bead 15.

Initial bead contact may be detected by a corresponding load cell transducer 13 at a base-end 111 of a wire 11 based on a fluctuation in forces transmitted through the wire 11 from an otherwise steady resting state RS (i.e., a zero-state, corresponding with a force input of approximately 0 N). Preferably, the fluctuation that triggers detection of an initial bead contact is one representing a deviation from the resting state RS that is in excess of a threshold background noise level. Optionally, initial bead contact may be identified by a surface embedded force sensor based on detection of a threshold force level at a surface of the moving bead 16 and/or by an internal electromagnetic sensor based on detection of a threshold change in an electromagnetic field at the moving bead 16.

A bead-to-bead impact occurs when a child draws a moving bead 16 along the corresponding wire 11 to eventually contact the stationary bead 15 affixed to the respective wire 11. Bead-to-bead impact may be detected by a corresponding load cell transducer 13 at a base-end 111 of the wire 11 based on a fluctuation in forces transmitted through the wire 11 representing a sudden inflection in a force input curve and/or a change in a magnitude of force-input that exceeds a threshold level that is predetermined to coincide with an impact of a moving bead 16 against a corresponding stationary bead 15. This can be seen in FIG. 2, which provides force curves for movement of a moving bead **16*a* along a straight wire 11*a* in the example shown in FIG. 1. Specifically, detection of the sudden inflection and significant increase in magnitude of the vertical force curve Fz at line B-B is indicative that moving bead 16*a* had been moved sufficiently in the vertical direction to impact the stationary bead 15*a***. Optionally, bead-to-bead impact may be identified by a surface embedded force sensor based on detection of a threshold force level and/or by an internal electromagnetic sensor based on detection of a threshold change in an electromagnetic field. Such embedded and/or electromagnetic sensors may also be used for effecting the motivational feedback system as discussed above, or may be provided separately from other sensors that are independently dedicated to effecting the motivational feedback system.

A trial duration TD, corresponding with a child's manipulation of a moving bead 16 along a single wire 11 is computed as the time from detection of an initial bead contact to detection of a bead-to-bead impact. The example in FIG. 2 represents forces measured for a single trial duration TD, corresponding with a child's manipulation of a single moving bead **16*a* from a time of initial bead contact (at line A-A) to a time of bead-to-bead impact (at line B-B). This illustrated example also includes measurement of forces during a post-trial (PT) period, following bead-to-bead impact. As shown in the example, over the course of a trial duration TD, there is measured each of a vertical force (Fz), along a vertical axis (Z) extending perpendicular to the base 10, and two horizontal forces (Fx, Fy), along two horizontal axes (X, Y) extending in parallel with the base 10 and perpendicular to one-another. Each of the measured forces is measured over the entire trial duration TD with generation of separate force curves for each measured force, following full-wave rectification around the resting state (0 N). In addition to the force curves shown in FIG. 2**, force impulses may also be measured in each direction, and a total force impulse for a trial duration TD may be calculated as the sum of the force impulses across the three force directions.

In use, a child will be instructed to grasp a moving bead 16 and draw it over the corresponding wire 11 until it contacts a stationary bead 15 affixed in place at a predetermined location on the wire 11. A child may be instructed to slide the moving bead 16 along a wire 11 several times, either at a self-selected 'comfort' speed, or as fast as possible. Forces exerted on the moving bead 16, and through the wire 11, are measured using one or more of the aforementioned sensing elements. The detection of relatively low forces on the beads 16/15 and through the wire 11 will be informative of a well-coordinated hand function, whereas a detection of relatively high forces will be informative of low hand function. The inclusion of wires 11 with a number of curves will result in increased difficulty in traversing a moving bead 16 along the wire 11, which is expected to further accentuate any deficiencies in hand function. More complex wire shapes may also provide further insights in hand function through time-based and force-based measures in completing the task.

Interrater reliability of the device 100 was assessed through testing with nine typically developing children aged 4-15 years. Two independent researchers analyzed and rated the output of the device, and a third researcher calculated intraclass correlation coefficients (ICC) between the analyses of the two researchers. For the trial duration measure, it was found that the ICC between the analyses (absolute agreement) was 0.97 for the low difficulty condition, 0.99 for the medium difficulty condition, and 0.99 for the high difficulty condition. For total force measure, it was found that the ICC between the two analyses was 0.99 for the low difficulty condition, 0.99 for the medium difficulty condition, and 0.98 for the high difficulty condition. These results evidence excellent interrater reliability of the device 100 in measuring precision force control for a wide age range of children and adolescents.

Devices and methods according to the present invention yield a number of benefits over conventional hand function test devices and methods. Whereas conventional tests focus primarily on the time and speed of task completion and/or observation of behavior, devices according to the present invention measure force data that cannot be reliably derived from a time-based test due to a weak correlation between speed and force measurements. While some conventional hand function tests may provide force measurements, those tests typically use devices that are unfamiliar and unappealing to children, resulting in lower engagement by a child during testing, and thus less informative test results. In contrast, devices according to the present invention adopt a toy-like design that draws the attention of children to yields a stronger engagement, resulting in more informative test results. In addition, adoption of a bead-on-wire assembly provides the inventive device with a configuration in which the moving parts are retained on the device itself. This has the added benefits of not only simplifying storage and handling of the device, but also making the device safe for use with small children by avoiding any potential for a choking hazard that may otherwise accompany tests that employ loose, small parts.

Although the present invention is described with reference to particular embodiments, it will be understood to those skilled in the art that the foregoing disclosure addresses exemplary embodiments only; that the scope of the invention is not limited to the disclosed embodiments;

and that the scope of the invention may encompass additional embodiments embracing various changes and modifications relative to the examples disclosed herein without departing from the scope of the invention as defined in the appended claims and equivalents thereto.

To the extent necessary to understand or complete the disclosure of the present invention, all publications, patents, and patent applications mentioned herein are expressly incorporated by reference herein to the same extent as though each were individually so incorporated.

The present invention is not limited to the exemplary embodiments illustrated herein, but is instead characterized by the appended claims, which in no way limit the scope of the disclosure.

What is claimed is:

1. A hand function testing device, comprising:

a base having a number of rigid wires protruding from a surface thereof, each rigid wire having a first end and a second end, and each rigid wire being accompanied by:

a stationary bead mounted at a fixed position on the rigid wire, the fixed position being intermediate of the first end and the second end, the stationary bead configured as a mechanical stop;

a moving bead movably mounted on the rigid wire, with movement of the moving bead limited to a working region of the rigid wire defined between the first end, as a base-end of the rigid wire, and the fixed position of the stationary bead mounted on the rigid wire, the moving bead being mounted on the rigid wire via reception of the rigid wire through a lumen in the moving bead; and at least one force sensing element for measuring a force input to the moving bead during a movement task of moving the moving bead along the working region of the rigid wire.

2. The hand function testing device according to claim 1, wherein the number of rigid wires comprises at least two rigid wires.

3. The hand function testing device according to claim 2, wherein the at least two rigid wires have working regions of different shapes from one another.

4. The hand function testing device according to claim 3, wherein the different shapes of the working regions are chosen from: a straight wire shape; a single-curve wire shape; and a multi-curve wire shape.

5. The hand function testing device according to claim 2, wherein the at least two rigid wires have working regions of different lengths from one another.

6. The hand function testing device according to claim 2, wherein the at least two rigid wires have different surface textures from one another.

7. The hand function testing device according to claim 2, wherein the at least two rigid wires have different overall dimensions from one another.

8. The hand function testing device according to claim 7, wherein the different overall dimensions of the rigid wires comprise at least different outer diameters from one another.

9. The hand function testing device according to claim 2, wherein a stationary bead on a first rigid wire is mounted at a first position along the first rigid wire, a stationary bead on a second rigid wire is mounted at a second position along the second rigid wire, the first and second positions being at different lengths along the respective rigid wires as measured from the base-ends of the respective rigid wires, thereby yielding different length working regions for the respective rigid wires.

10. The hand function testing device according to claim 2, wherein at least one moving bead on a first rigid wire and at least one moving bead on a second rigid wire have different surface textures from one another.

11. The hand function testing device according to claim 2, wherein at least one moving bead mounted on a first rigid wire and at least one moving bead mounted on a second rigid wire have different overall dimensions from one another.

12. The hand function testing device according to claim 11, wherein the different overall dimensions of the moving beads comprise at least different outer diameters from one another.

13. The hand function testing device according to claim 11, wherein the different overall dimensions of the moving beads comprise at least a difference in the dimensions of the lumens of the respective beads.

14. The hand function testing device according to claim 1, wherein there are at least three rigid wires, each rigid wire having at least one difference in overall configuration from the overall configurations of the other two rigid wires.

15. The hand function testing device according to claim 1, wherein at least one rigid wire has two or more moving beads mounted thereon.

16. The hand function testing device according to claim 1, wherein there are at least three rigid wires, each rigid wire having at least one moving bead mounted thereon that has a different overall configuration from the overall configurations of at least one moving bead mounted on each of the other two rigid wires.

17. The hand function testing device according to claim 1, wherein the at least one force sensing element comprises a sensor positioned at the base-end of the at least one rigid wire, the force sensing element adapted to measure a force input to the moving bead based on transmission of an input force applied to the moving bead through the rigid wire to the force sensing element.

18. The hand function testing device according to claim 17, wherein the sensor positioned at the base-end of the at least one rigid wire is a strain-gauge load cell transducer.

19. The hand function testing device according to claim 1, wherein the at least one force sensing element comprises at least one sensor embedded in at least one of the moving bead and the stationary bead.

20. The hand function testing device according to claim 19, wherein the at least one sensor is a force-sensing flexible resistor embedded at a surface of the moving bead and/or the stationary bead, the force-sensing flexible resistor being adapted to measure a bead-to-bead contact force.

21. The hand function testing device according to claim 19, wherein the at least one sensor is a force-sensing flexible resistor embedded at a surface of the moving bead, the force-sensing flexible resistor being adapted to measure a user's gripping contact force applied against the surface of the moving bead.

22. The hand function testing device according to claim 19, wherein the at least one sensor is an electromagnetic sensor embedded internally within the moving bead and/or the stationary bead, the electromagnetic sensor being adapted to detect a change in electromagnetic field at the respective bead.

23. The hand function testing device according to claim 1, wherein the at least one force sensing element is adapted to measure a force input to the moving bead in three separate axes (Fx, Fy, Fz).

24. The hand function testing device according to claim 1, wherein the at least one force sensing element is adapted to measure a change in position of the moving bead.

25. The hand function testing device according to claim 1, wherein at least two force sensing elements accompany at least one of the number of rigid wires.

26. The hand function testing device according to claim 25, wherein at least one of the number of rigid wires is accompanied by at least three force sensing elements, comprising:

a first sensor positioned at the base-end of the rigid wire;

a second sensor embedded in the moving bead mounted on the rigid wire; and a third sensor embedded in the stationary bead mounted on the rigid wire.

27. The hand function testing device according to claim 1, further comprising a feedback system that provides a pre-recorded sensory feedback upon determining that a predetermined task has been completed with the testing device.

28. The hand function testing device according to claim 27, wherein the feedback system is configured to receive signals from the at least one force sensing element for triggering the pre-recorded sensory feedback.

29. The hand function testing device according to claim 27, wherein the feedback system is configured to determine that a predetermined task has been completed upon detecting a bead-to-bead contact.

30. The hand function testing device according to claim 27, wherein the pre-recorded sensory feedback comprises at least one signal chosen from: an audio signal, a visual signal, and a somatosensory signal.

31. The hand function testing device according to claim 1, further comprising:

a non-transitory storage medium configured to receive and store force data measured by the at least one force sensing element.

32. The hand function testing device according to claim 31, wherein the storage medium is configured to generate a force analysis based on measured force data.

33. The hand function testing device according to claim 32, wherein the force analysis comprises one or more force readings generated during a trial duration for performance of a predetermined task with the testing device.

34. The hand function testing device according to claim 33, wherein the storage medium is configured to identify movement of the moving bead of one of the number of rigid wires to cause a bead-to-bead contact as a predetermined task for the generation of force readings.

35. The hand function testing device according to claim 34, wherein the storage medium is configured to identify a start of a trial duration upon detection of an initial contact force at the moving bead, and to identify an end of a trial duration upon detection of a bead-to-bead contact.

36. The hand function testing device according to claim 34, wherein the storage medium is configured to generate a force analysis comprising force measurements of input forces applied to the moving bead along three separates axes (Fx, Fy, Fz).

37. The hand function testing device according to claim 36, wherein the storage medium is configured to generate a force analysis that further comprises force impulses along the three separates axes.

38. The hand function testing device according to claim 37, wherein the storage medium is configured to generate a force analysis comprising a total force impulse as a sum of the force impulses along the three separates axes.

39. A method of testing hand function, comprising:

utilizing the hand function testing device according to claim 1 to:

measure, via the at least one force sensing element, force inputs applied to at least one moving bead during performance of a predetermined task; and generate, via a non-transitory storage medium of the hand function testing device, a force analysis based on the force inputs measured by the at least one force sensing element.

40. The method of testing hand function according to claim 39, wherein the predetermined task comprises moving the moving bead of one of the number of rigid wires to cause a bead-to-bead contact.

41. The method of testing hand function according to claim 40, wherein the force inputs are measured during a trial duration that begins upon detection of an initial contact force in excess of a predetermined threshold force level at the moving bead and ends upon detection of a bead-to-bead contact.

42. The method of testing hand function according to claim 40, wherein the force analysis comprises measurements of input forces applied to the moving bead, the force measurements being measured along three separates axes (Fx, Fy, Fz).

43. The method of testing hand function according to claim 42, wherein the force analysis further comprises force impulses along the three separates axes.

44. The method of testing hand function according to claim 43, wherein the force analysis further comprises a total force impulse as a sum of the force impulses along the three separates axes.

45. The method of testing hand function according to claim 39, wherein the predetermined task comprises moving the moving bead of a first one of the number of rigid wires to cause a bead-to-bead contact, and moving the moving bead of a second one of the number of rigid wires to cause a bead-to-bead contact; and a first force analysis is generated from the force inputs applied to the moving bead of the first one of the number of rigid wires, and a second force analysis is generated from the force inputs applied to the moving bead of the second one of the number of rigid wires.

46. A method of making a hand function testing device according to claim 1, comprising:

providing the base and the number of rigid wires, with the rigid wires separate from the base and configured for mounting on the base.

47. A method of making a hand function testing device according to claim 1, comprising:

mounting the number of rigid wires to the base.

* * * * *